(12) United States Patent
Shim et al.

(10) Patent No.: US 12,066,512 B2
(45) Date of Patent: Aug. 20, 2024

(54) SYSTEMS AND METHODS FOR RAPIDLY DETERMINING ONE OR MORE METABOLITE MEASUREMENTS FROM MR SPECTROSCOPY DATA

(71) Applicants: Emory University, Atlanta, GA (US); University of Miami, Miami, FL (US)

(72) Inventors: Hyunsuk Shim, Atlanta, GA (US); Lee Cooper, Atlanta, GA (US); Saumya Gurbani, Atlanta, GA (US); Andrew Maudsley, Miami, FL (US); Sulaiman Sheriff, Miami, FL (US)

(73) Assignees: Emory University, Atlanta, GA (US); University of Miami, Miami, FL (US)

( * ) Notice: Subject to any disclaimer, the term of this patent is extended or adjusted under 35 U.S.C. 154(b) by 294 days.

(21) Appl. No.: 17/295,528

(22) PCT Filed: Nov. 20, 2019

(86) PCT No.: PCT/US2019/062492
§ 371 (c)(1),
(2) Date: May 20, 2021

(87) PCT Pub. No.: WO2020/106896
PCT Pub. Date: May 28, 2020

(65) Prior Publication Data
US 2022/0018922 A1 Jan. 20, 2022

Related U.S. Application Data

(60) Provisional application No. 62/769,842, filed on Nov. 20, 2018.

(51) Int. Cl.
*G01R 33/485* (2006.01)
*G01R 33/46* (2006.01)
(Continued)

(52) U.S. Cl.
CPC ....... *G01R 33/485* (2013.01); *G01R 33/4625* (2013.01); *G06N 3/045* (2023.01); *G06N 3/084* (2013.01)

(58) Field of Classification Search
None
See application file for complete search history.

(56) References Cited

U.S. PATENT DOCUMENTS 5,121,443 A * 6/1992 Tomlinson ......... G01N 30/8624
73/23.23
5,218,529 A * 6/1993 Meyer ...................... G06N 3/02
706/924
(Continued)

FOREIGN PATENT DOCUMENTS

WO WO2018045274 A1 3/2018
WO WO2018106713 A1 6/2018

OTHER PUBLICATIONS

Abadi et al. "TensorFlow: A System for Large-Scale Machine Learning." OSDI'16: Proceedings of the 12th USENIX Symposium on Operating Systems Design and Implementation, 2016; 265-283.
(Continued)

*Primary Examiner* — Rodney E Fuller
(74) *Attorney, Agent, or Firm* — Emory Patent Group

(57) ABSTRACT

Systems and methods provide a parallelized deep learning approach to spectral fitting for magnetic resonance spectroscopy data enabling accurate and rapid spectral fitting and determination of metabolite measurements using a conventional computer. The method may include processing multi-spectra magnetic resonance (MR) spectroscopy data of a region of interest through a series of neural networks. The method may include determining baseline components of each spectrum using a first neural network of the series, generating baseline-corrected components for each spectrum using the baseline components; and determining one or (Continued)

more peak components of each spectrum using a second neural network of the series and the baseline-corrected components. The method may further include determining one or more metabolite measurements of the one or more metabolites in the region of interest using the one or more peak components.

20 Claims, 9 Drawing Sheets

(51) Int. Cl.
G06N 3/045 (2023.01)
G06N 3/084 (2023.01)

(56) References Cited

U.S. PATENT DOCUMENTS

| | | | | |
|---|---|---|---|---|
| 5,887,588 | A | * | 3/1999 | Usenius ............. G16H 50/20 706/924 |
| 6,617,169 | B2 | * | 9/2003 | Ke ..................... G01N 33/9426 324/309 |
| 9,589,374 | B1 | | 3/2017 | Gao et al. |
| 9,673,030 | B2 | * | 6/2017 | Jones ..................... G16B 40/00 |
| 9,799,120 | B1 | | 10/2017 | Fenchel et al. |
| 2009/0247860 | A1 | | 10/2009 | Djuric et al. |
| 2016/0162782 | A1 | | 6/2016 | Park |
| 2018/0180537 | A1 | | 6/2018 | Diem et al. |
| 2018/0289323 | A1 | | 10/2018 | Labyed et al. |
| 2019/0307393 | A1 | | 10/2019 | Lotz et al. |
| 2021/0169332 | A1 | | 6/2021 | Zimmerman et al. |

OTHER PUBLICATIONS

Bhat et al. "Fast quantification of proton magnetic resonance spectroscopic imaging with artificial neural networks." Journal of Magnetic Resonance, 2006; 183:110-122.

Cordova et al. "Whole-brain spectroscopic MRI biomarkers identify infiltrating margins in glioblastoma patients." Neuro-Oncology, 2016; 18(8):1180-1189.

Cordova et al. "A Systematic Pipeline for the Objective Comparison of Whole-Brain Spectroscopic MRI with Histology in Biopsy Specimens from Grade 3 Glioma." Tomography, 2016; 2(2):106-116.

Cudalbu et al. "Handling Macromolecule Signals in the Quantification of the Neurochemical Profile." Journal of Alzheimer's Disease, 2012; 31:S101-S115.

Donoho et al. "Adapting to Unknown Smoothness via Wavelet Shrinkage." Journal of the American Statistical Association, 1995; 90:1200-1224.

Griswold et al. "Generalized Autocalibrating Partially Parallel Acquisitions (GRAPPA)." Magnetic Resonance in Medicine, 2002; 47:1202-1210.

Gurbani et al. "A convolutional neural network to filter artifacts in spectroscopic MRI." Magnetic Resonance in Medicine, 2018; 80:1765-1775.

Gurbani et al. "A Feasibility Study of Radiation Therapy Dose Escalation Guided By Spectroscopic Magnetic Resonance Imaging in Patients with Glioblastoma." International Society For Magnetic Resonance in Medicine, ISMRM, Jun. 2018; No. 1155.

Hatami et al. "Magnetic Resonance Spectroscopy Quantification Using Deep Learning." MICCAI, 2018; 467-475.

LeCun et al. "Deep learning." Nature, 2015; 521:436-444.

Li et al. "An advanced MRI and MRSI data fusion scheme for enhancing unsupervised brain tumor differentiation." Computers in Biology and Medicine, 2017; 81:121-129.

Maudsley et al. "Mapping of Brain Metabolite Distributions by Volumetric Proton MR Spectroscopic Imaging (MRSI)." Journal of Magnetic Resonance, 2009; 61:548-559.

McKnight et al. "Histopathological validation of a three-dimensional magnetic resonance spectroscopy index as a predictor of tumor presence." Journal of Neurosurgery, 2002; 97:794-802.

Sabati et al. "Multivendor Implementation and Comparison of Volumetric Whole-Brain Echo-Planar MR Spectroscopic Imaging." Magnetic Resonance in Medicine, 2015; 74:1209-1220.

Saudek et al. "Analysis of Human Brain NMR Spectra in Vivo Using Artificial Neural Networks." Artificial Neural Networks—ICANN 2008. Lecture Notes in Computer Science, 2008; 5164:517-526.

Soher et al. "Automated Spectral Analysis III: Application to in Vivo Proton MR Spectroscopy and Spectroscopic Imaging." Magnetic Resonance in Medicine, 1998; 40:822-831.

Young et al. "Automated Spectral Analysis II: Application of Wavelet Shrinkage for Characterization of Non-Parameterized Signals." Magnetic Resonance in Medicine, 1998; 40:816-821.

Extended European Search Report for EP Application No. 19886588.3 dated Jun. 29, 2022.

International Search Report and Written Opinion for PCT Application No. PCT/US2019/062492 dated Nov. 20, 2019.

* cited by examiner

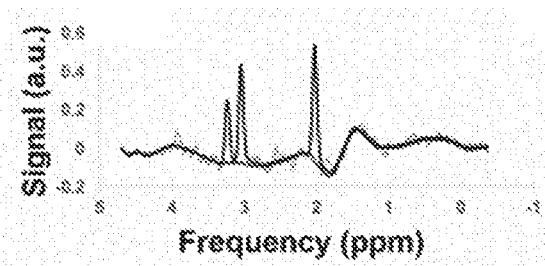
FIG. 4A
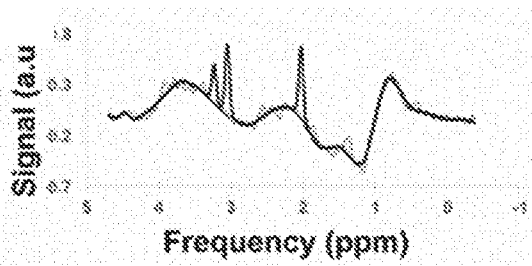
FIG. 4B
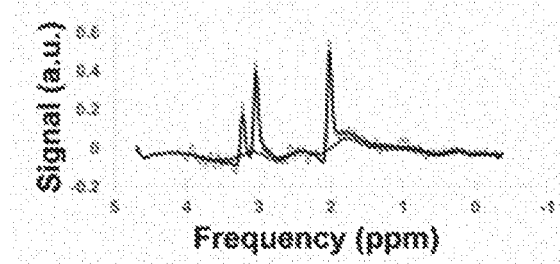
FIG. 4C
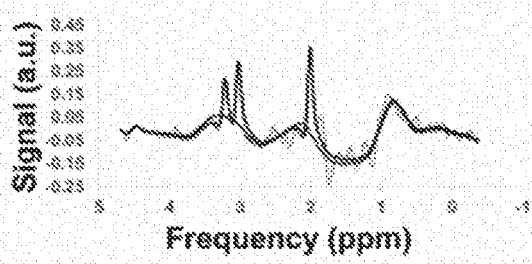
FIG. 4D
——Spectrum ——Baseline ——Baseline + Peak
FIG. 4E

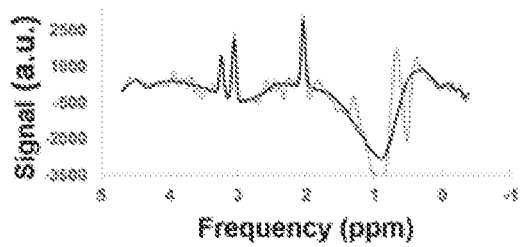
FIG. 5A
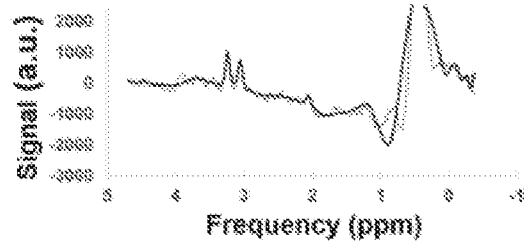
FIG. 5B
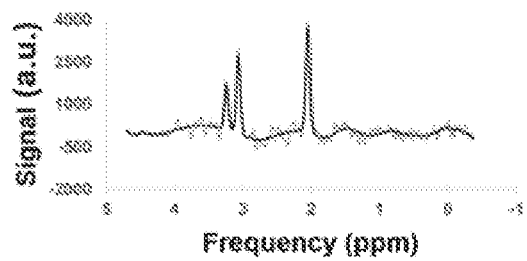
FIG. 5C
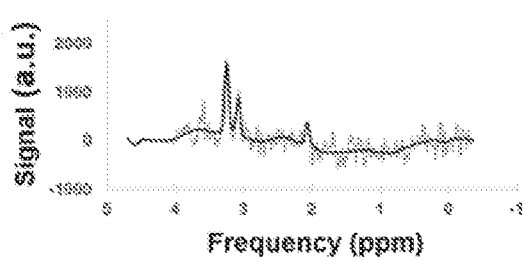
FIG. 5D
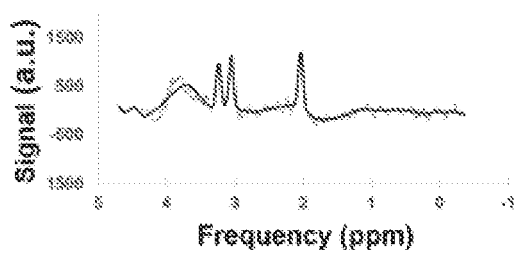
FIG. 5E
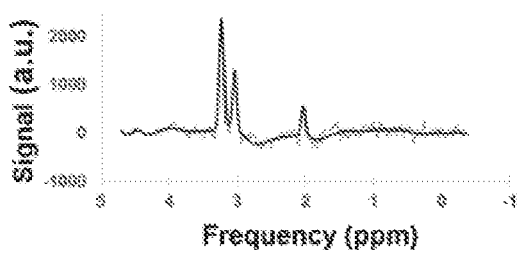
FIG. 5F
— Spectrum — Fitted
FIG. 5G

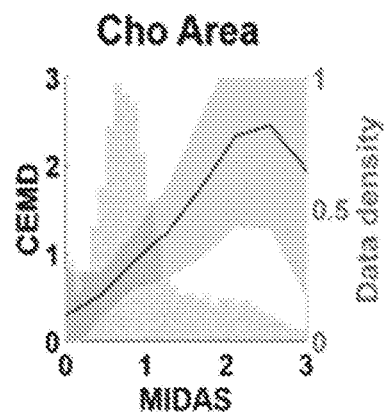
FIG. 6A
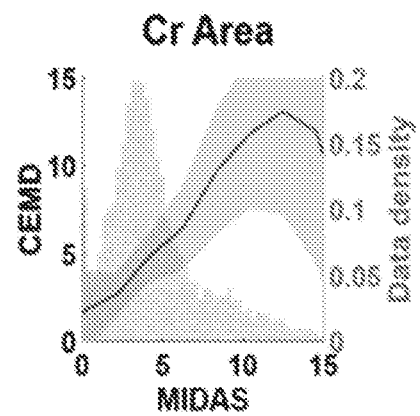
FIG. 6B
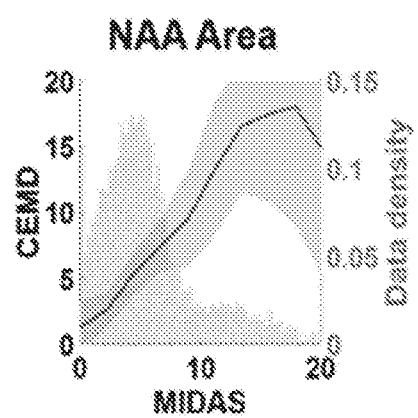
FIG. 6C
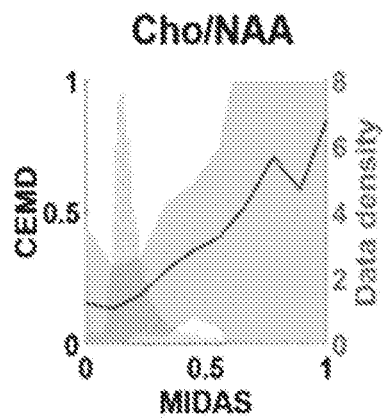
FIG. 6D
— Mean    +/- 1 Std. Dev.    Histogram
FIG. 6E

FIG. 7A
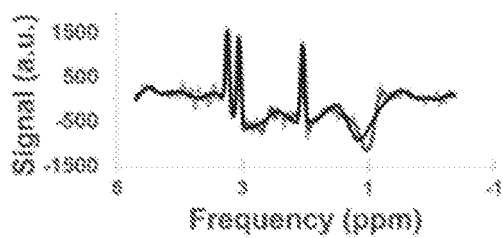
FIG. 7B
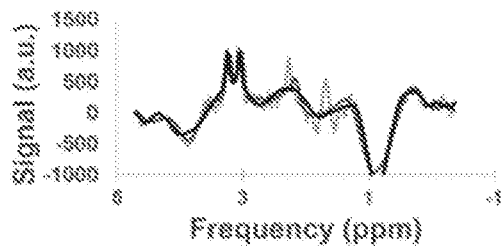
FIG. 7C
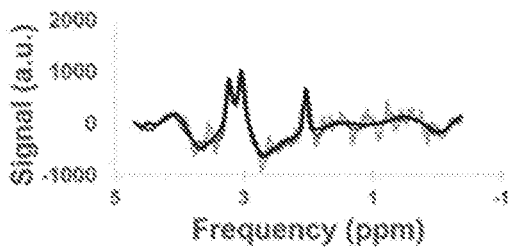
FIG. 7D
— MIDAS  — CEMD
FIG. 7E
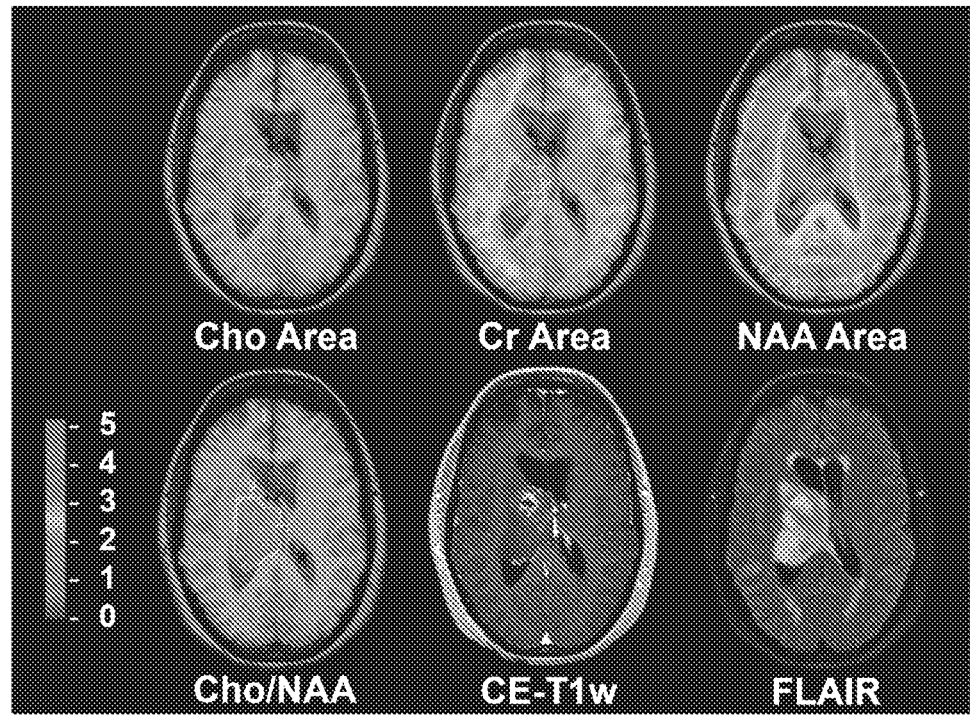
FIG. 8

| Subject | CEMD Time (sec) | 2x Cho/NAA Vol. (cm³) | | Volume Difference (cm³) | DSC | Z Test P Value |
|---|---|---|---|---|---|---|
| | | CEMD | MIDAS | | | |
| 1 | 17.8 | 57.9 | 56.7 | 1.2 | 0.84 | 0.047 |
| 2 | 26.3 | 31.9 | 35.1 | -3.2 | 0.56 | 0.410 |
| 3 | 18.1 | 72.2 | 76.0 | -3.8 | 0.87 | 0.026 |
| 4 | 21.0 | 35.9 | 39.9 | -4.1 | 0.65 | 0.265 |
| 5 | 17.4 | 23.0 | 39.6 | -16.7 | 0.64 | 0.277 |
| 6 | 23.0 | 5.9 | 4.0 | 1.8 | 0.59 | 0.366 |
| 7 | 19.0 | 105.2 | 134.1 | -28.8 | 0.86 | 0.037 |
| 8 | 20.4 | 86.9 | 60.0 | 26.9 | 0.75 | 0.141 |
| 9 | 20.1 | 54.9 | 22.8 | 32.1 | 0.57 | 0.385 |
| 10 | 23.1 | 37.7 | 30.7 | 7.0 | 0.81 | 0.072 |
| | | | | | | |
| Mean | 20.6 | --- | --- | 1.2 | 0.72 | --- |
| Std. Dev | 2.8 | --- | --- | 18.1 | 0.13 | --- |

FIG. 9

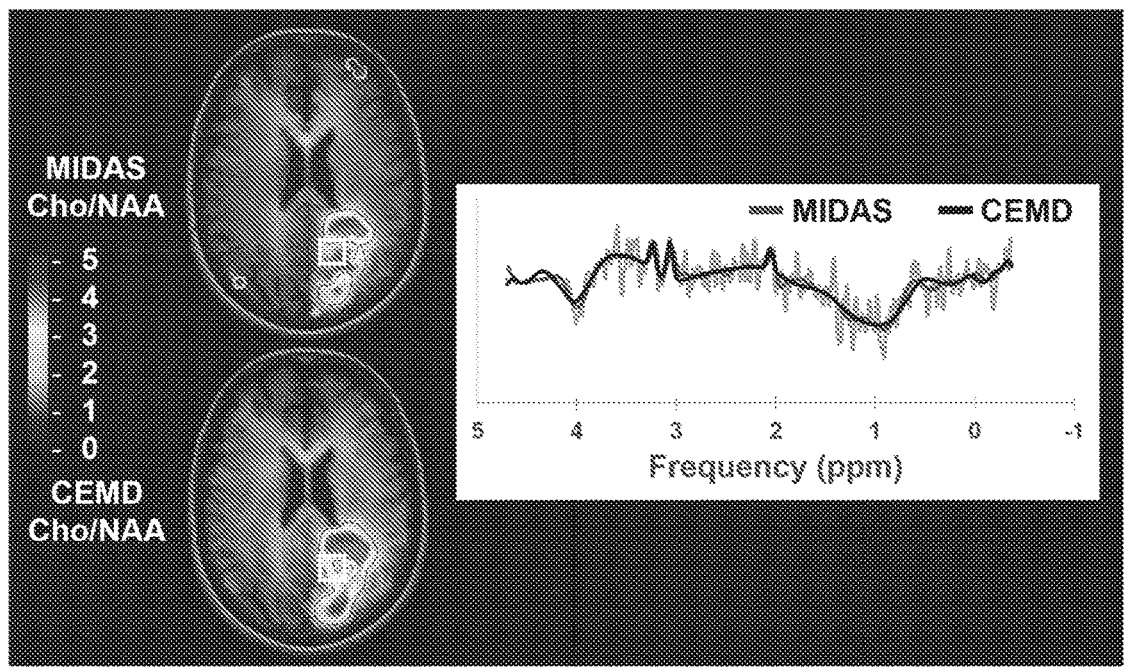
FIG.10
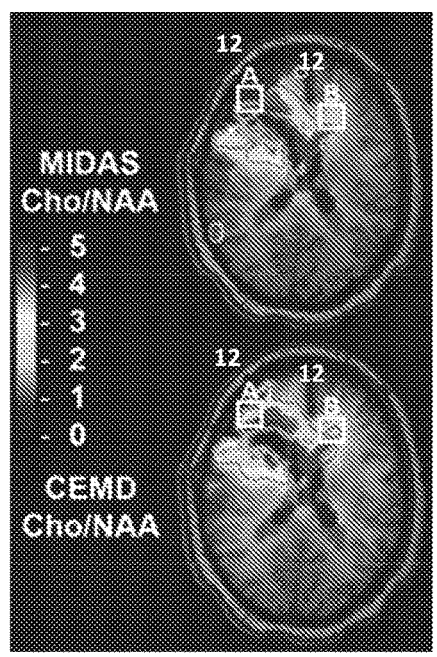
FIG.11
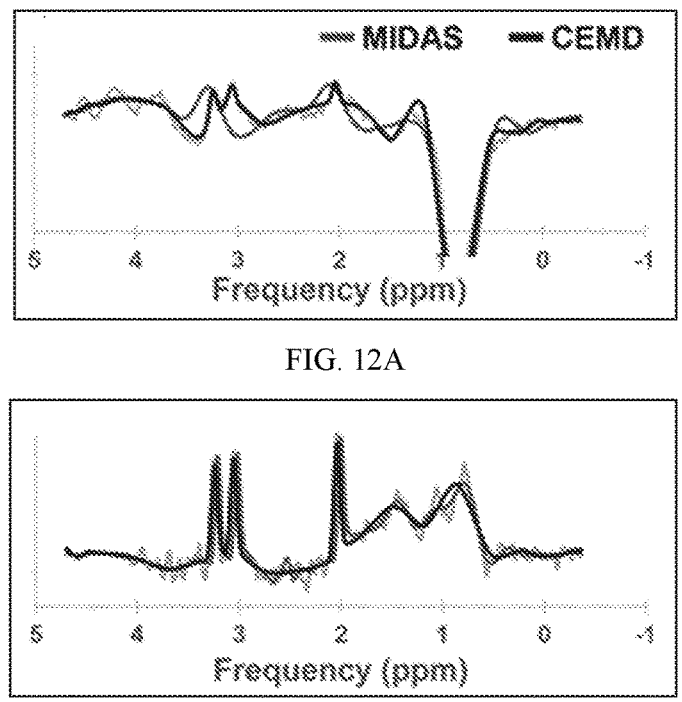
FIG. 12A
FIG. 12B

SYSTEMS AND METHODS FOR RAPIDLY DETERMINING ONE OR MORE METABOLITE MEASUREMENTS FROM MR SPECTROSCOPY DATA

CROSS-REFERENCE TO RELATED APPLICATIONS

This application is the National Stage of International Application No. PCT/US2019/062492 filed Nov. 20, 2019, which claims the benefit of U.S. Provisional Application No. 62/769,842 filed Nov. 20, 2018. The entirety of each of these applications is hereby incorporated by reference for all purposes.

STATEMENT REGARDING FEDERALLY SPONSORED RESEARCH OR DEVELOPMENT

This invention was made with government support under EB028145 awarded by the National Institutes of Health. The government has certain rights in the invention.

BACKGROUND

Proton spectroscopic magnetic resonance imaging (later referred to as "spectroscopic MRI") is an imaging modality capable of generating high-resolution 3D mapping of cerebral metabolites concentrations in vivo. Spectroscopic MIII has shown great promise in the detection and monitoring of neurologic pathologies such as tumor based on these concentrations. Currently available methods of quantitation of metabolites are generally iterative optimization procedures to find the model parameters that best match the data However, these methods do no scale well to volumetric spectroscopic imaging, which can contain 10,000 to 100,000 spectra in a whole-brain scan. In such cases, spectral fitting can require significant processing time on a high performance workstation resulting in a computational bottleneck. This computation bottleneck prevents on-scanner processing and rapid turnaround needed for clinical applications, such as guiding radiotherapy planning.

SUMMARY

Thus, there is a need for timely and accurate imaging processing, including spectral fitting.

The systems and methods of the disclosure provide rapid and accurate spectral fitting for magnetic resonance spectroscopy data enabling spectral fitting and (in vivo) metabolite measurements that can be performed, for example, using a conventional computer. The disclosure can thereby enable on-scanner processing. This can thereby increase the implementation and usefulness of whole-brain MR spectroscopy in the clinical workflow, such as detection of brain pathologies (e.g., tumors, inflammatory conditions (e.g., traumatic brain injury), etc.), radiation therapy planning, and the like.

In some embodiments, the methods may include a method for determining a concentration of one or more metabolites within a region of interest. The method may include processing magnetic resonance (MR) spectroscopy data of a region of interest. The magnetic resonance spectroscopy data may include a plurality of spectra and one or more metabolites through a series of neural networks. In some embodiments, the processing may include determining baseline components of each spectrum using a first neural network of the series. The baseline components may define a baseline model. The processing may further include generating baseline-corrected components for each spectrum using the baseline components. The processing may further include determining one or more peak components of each spectrum using a second neural network of the series and the baseline-corrected components. The method may further include determining one or more metabolite measurements of the one or more metabolites in the region of interest using the one or more peak components:

In some embodiments, the method may further include determining one or more spectral features of each peak region using the one or more peak components. In some embodiments, the one or more metabolite measurements may be determined using the one or more spectral features.

In some embodiments, the method may include generating one or more maps of the region of interest using the one or more metabolites and/or one or more metabolite measurements and corresponding anatomical MR data. In some embodiments, the method may include registering the one or more metabolites and/or the one or more metabolite measurements with corresponding anatomical MR data.

In some embodiments, the systems may include a system for determining a concentration of one or more metabolites within a region of interest. The system may include one or more processors. The system may further include one or more hardware storage devices having stored thereon computer-executable instructions which are executable by the one or more processors to cause the computing system to perform at least processing magnetic resonance (MR) spectroscopy data of a region of interest. The magnetic resonance spectroscopy data may include a plurality of spectra and one or more metabolites through a series of neural networks. The processing may include determining baseline components of each spectrum using a first neural network of the series. The baseline components may define a baseline model. The processing may further include generating baseline-corrected components for each spectrum using the baseline components, and determining one or more peak components of each spectrum using a second neural network of the series and the baseline-corrected components. The one or more processors may be further configured to cause the computing system to perform determining one or more metabolite measurements of the one or more metabolites in the region of interest using the one or more peak components.

In some embodiments, the one or more processors may be further configured to cause the computing system to perform at least determining one or more spectral features of each peak region using the one or more peak components. The one or more metabolite measurements may be determined using the one or more spectral features.

In some embodiments, the one or more processors may be further configured to cause the computing system to perform at least generating one or more maps of the region of interest using the one or more metabolites and/or one or more metabolite measurements and corresponding anatomical MR data. In some embodiments, the one or more processors may be further configured to cause the computing system to perform at least registering the one or more metabolites and/or the one or more metabolite measurements with corresponding clinical anatomical MR data.

In some embodiments, the one or more metabolite measurements may include a quantification of concentration of the one more metabolites, a concentration ratio between at least two metabolites, a chemical exchange rate between at least two metabolites, among others, or a combination thereof.

In some embodiments, the region of interest may be a portion of a brain. The one or more metabolites may include choline (Cho) and N-acetylaspartate (NAA). The one or more metabolite measurements may include a Cho/NAA ratio.

In some embodiments, the first neural network may include a trained encoder and a decoder. The trained encoder may determine a plurality of baseline parameters. The decoder defined by wavelet reconstruction equations may determine the baseline components for each spectrum using the baseline parameters.

In some embodiments, the second neural network may include a trained encoder and a decoder. The trained encoder may determine a plurality of peak parameters. The decoder defined by a Lorentzian-Gaussian lineshape model may determine the peak components for each spectrum using the plurality of peak parameters.

In some embodiments, the one or more peak parameters may include one or more spectral features for each metabolite; zero-order phase, first-order phase, gaussian decay constant and Lorentzian decay constant.

In some embodiments, the magnetic resonance spectroscopy data may be processed and provided in a first matrix. The first matrix may include a plurality of datapoints for each spectrum. The plurality of datapoints representing an entire model for each spectrum;

In some embodiments, the determining the baseline components may include generating a second matrix. The second matrix may include the baseline components for each spectrum.

In some embodiments, the determining the base-line corrected components may include generating a third matrix. The third matrix may include the base-line corrected datapoints for each spectrum.

In some embodiments, the determining the one or more peak components may include generating a fourth matrix. The fourth matrix may include the one or more peak components for each spectrum.

In some embodiments, each of the first matrix, second matrix, third matrix, and fourth matrix may be a 2D matrix. Each row of each matrix may represent each spectrum.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, the emphasis being placed upon illustrating the principles of the disclosure.

FIGS. 4A-E show examples of spectral fittings generated by a system implementing the convolutional encoder-model decoder ("CEMD") architecture according to embodiments;

FIG. 4A shows a first example of spectral fittings generated by a system according to embodiments; FIG. 4B shows a second example of spectral fittings generated by a system according to embodiments; FIG. 4C shows a third example of spectral fittings generated by a system according to embodiments; FIG. 4D shows a fourth example of spectral fittings generated by a system according to embodiments; and FIG. 4E shows a legend for the examples shown in FIGS. 4A-D;

FIGS. 5A-G show examples of sample spectra (real components) from scans of subjects with glioblastoma; FIGS. 5A and B show sample spectra (real components) from regions of healthy tissue and tumor, respectively, of a Subject 1; FIGS. 5C and D show sample spectra (real components) from regions of healthy tissue and tumor, respectively, of a Subject 2; FIGS. 5E and F show sample spectra (real components) from regions of healthy tissue and tumor, respectively, of a Subject 3; and FIG. 5G shows a legend for the examples shown in FIGS. 5A-F;

FIGS. 6A-6E show examples of a comparison of metabolite values computed by Metabolite Imaging and Data Analysis System ("MIDAS") and the CEMD system; FIG. 6A shows a comparison of Cho Area; FIG. 6B shows a comparison of CR Area; FIG. 6C shows a comparison of NAA Area; FIG. 6D shows a comparison of a Cho/NAA ratio used for tumor detection; and FIG. 6E shows a legend for the examples shown in FIGS. 6A-D;

FIGS. 7A-E show examples of comparisons of MIDAS and CEMD spectral fittings on challenging spectra; FIG. 7A shows a first comparison example of spectral fittings; FIG. 4B shows a second comparison example of spectral fittings; FIG. 7C shows a third comparison example of spectral fittings; FIG. 7D shows a comparison example of spectral fittings; and FIG. 7E shows a legend for the examples shown in FIGS. 7A-D;

FIG. 8 shows examples of whole-brain metabolite maps generated by CEMD for a patient with glioblastoma;

FIG. 9 shows a table of a subject-wise comparison of Cho/NAA abnormality volumes that were contoured for CEMD and MIDAS fitting and the results;

FIG. 10 shows an example of a comparison of the metabolite maps and Cho/NAA volumes generated by MIDAS and CEMD in a subject with glioblastoma;

FIG. 11 shows another example of a comparison of the metabolite maps generated by MIDAS and CEMD in a subject with glioblastoma;

FIGS. 12A and 12B show the comparison of Cho/NAA volumes generated by MIDAS and CEMD for regions 12A and 12B of FIG. 11, respectively.

DESCRIPTION OF THE EMBODIMENTS

Figure 1:
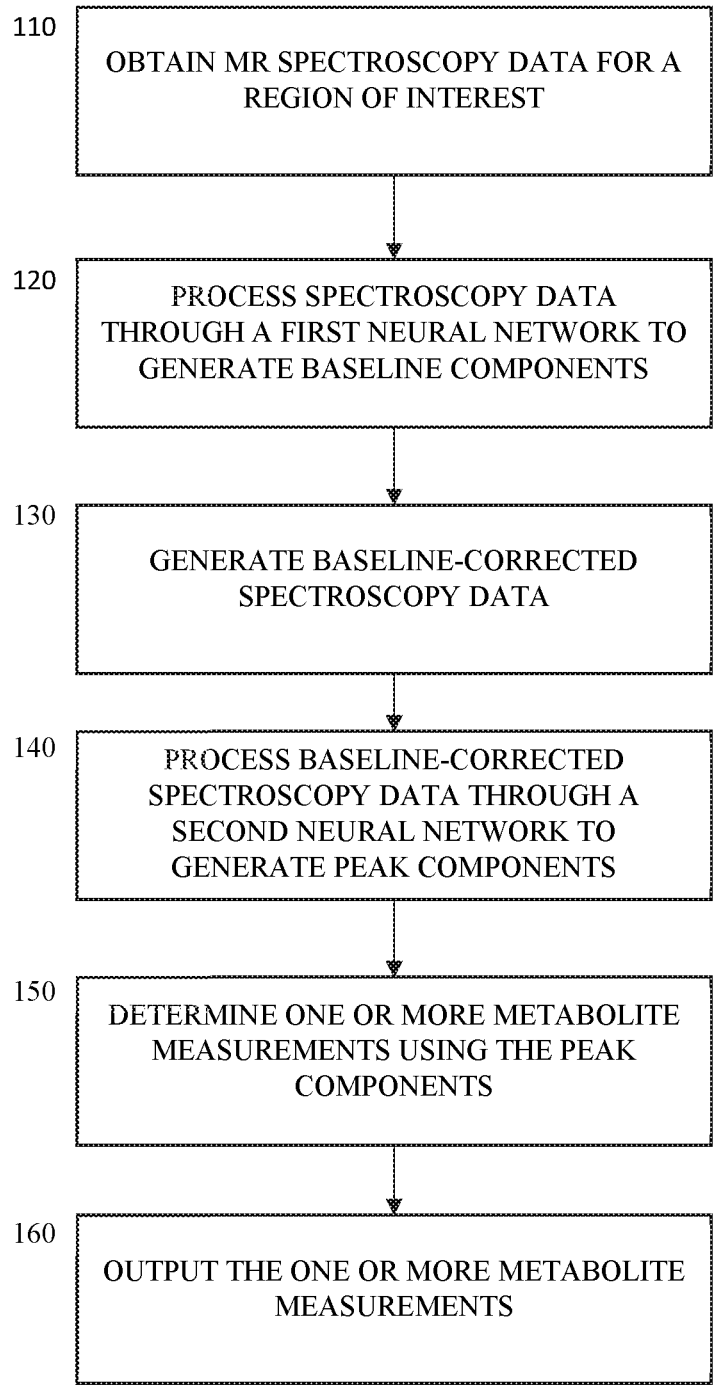
FIG. 1 shows an example of a method for determining one or more metabolite measurements from MR spectroscopic data according to embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The systems and methods of the disclosure provide a parallelized deep learning approach to spectral fitting for magnetic resonance spectroscopy data enabling spectral fitting and (in vivo) metabolite measurements to be performed in substantially real-time (e.g., in about one minute), for example, using a conventional computer. The disclosure uses an unsupervised deep learning architecture that incorporates mathematical and physics-based models of spectral lines shape and baseline to generate an encoding of spectral parameters while being fully constrained within known physics. The architecture includes a series of linear operations and therefore is highly parallelizable. Multiple spectra acquired using a magnetic resonance spectroscopy system can be combined in a (2D) matrix (e.g. rows including datapoints representing each spectrum) and passed through the architecture according to the disclosure to generate independent parameter sets on each spectrum in parallel, resulting in spectral fitting and metabolite quantification (e.g., concentration or volume), for example, of the region of interest (e.g., whole-brain, an anatomic region within the brain, etc.), in substantially real-time without requiring substantial computational processing resources (e.g., graphical processing units (GPUs)). The disclosure can thereby address the computational bottleneck in processing of (in vivo) whole-brain spectroscopic imaging provided by currently available methods.

The reduced computational processing requirements and substantially real-time spectral fitting provided by the disclosure can greatly benefit the clinical adoption of whole-brain MR spectroscopy. By way of example, the architecture according to the disclosure could be implemented on-board scanner computers, enabling real-time reconstruction and review of metabolic data without the need for offloading of data to a secondary machine or cluster for further processing. This can enable fitted data and determined metabolite volumes to be evaluated in substantially real-time for quality assurance (e.g., determine if a scan needs to repeated), be sent to clinical PACS systems in a much more streamlined fashion; more quickly viewed and analyzed by a clinician.

While some example of the disclosure may be specific to region(s) of the brain, it will be understood that these examples are nonlimiting and that the methods and systems may be performed for other parts of the body. Additionally, while some example of the disclosure may be specific to magnetic resonance spectroscopy imaging (MRSI), it will be understood that these examples are also nonlimiting and that the methods and systems may also be applied to other types of MR spectroscopy imaging, including but not limited to magnetic resonance spectroscopy (MRS), among others, or a combination thereof. Further, while some example of the disclosure may be specific to quantifying cerebral metabolites for one or more regions of the brain for analysis of specific neurologic pathologies (e.g., tumor such as glioblastoma), it will be understood that these examples are also nonlimiting and that the methods and systems may also be used for analysis of other neurologic pathologies, including but not limited to inflammatory conditions (e.g., traumatic brain injury), other brain tumors, among others, or any combination thereof.

In some embodiments, "metabolite", as used herein, can include any exogenous or endogenous chemical substance, or chemical reaction products from these substances. Metabolites can be, but are not limited to, iron, glucose, amino acids, nucleotides, vitamins, antioxidants, proteins, and lipids. For example, a metabolite may include but are not limited to creatine, phosphocreatine, N-acetylaspartate (NAA), choline, lipids, lactate, myo-insoitol, glutamate, glutamine, among others, or any combination thereof. By way of example, for evaluating patients with glioblastoma, the metabolites may include but are not limited to choline (Cho) and N-acetylaspartate (NAA).

FIG. 1 shows a method 100 of determining one or more measurements of one or more metabolites associated with a region of interest using magnetic resonance spectroscopy data of that region of a subject according to embodiments.

In some embodiments, the method 100 may include a step 110 of obtaining magnetic resonance (MR) spectroscopy data of a region of interest of a subject. For example, if evaluating a subject for a neurologic pathology, such as glioblastoma, the region of interest may be a region of the brain. In some embodiments, the region of the brain may include the whole-brain or a portion of the brain, such as an anatomic region of the brain.

In some embodiments, the MR spectroscopy data may be acquired using any available magnetic resonance system capable of acquiring MR spectroscopy data, such as a 3T MRI scanner. In some embodiments, the data may be acquired using one or more MR protocols or parameters (e.g., pulse sequence, flip angle ("FA"), RF pulse phase, TR, echo time ("TE"), sampling patterns, etc.). In some embodiments, the one or more MR protocols/parameters may be specific to the metabolite(s) to be measured and/or region(s) of interest to be scanned/imaged. By way of example, the one or more protocols may be specific to proton spectroscopic magnetic resonance imaging (sMRI) or other non-invasive MR spectroscopic modalities capable of generating volumetric maps of in vivo tissue metabolism of the region of interest (e.g., brain) without the need for ionizing radiation or injected contrast agent.

By way of example, the data may be acquired using magnetic resonance spectroscopy protocols for imaging multiple-voxels within a region of interest (rather than measuring metabolite signal in a single voxel), such as proton spectroscopic magnetic resonance imaging (e.g., MRS or MRSI) that can enable multi-voxel volumes of metabolite levels to be obtained in vivo without contrast agents or radioactive tracers. For example, the MR spectroscopy data may be acquired using an echo-planar spectroscopic imaging (EPSI) sequence, such as those described in Cordova J S, Gurbani S S, Olson J J, Liang Z, Cooper L A D, Shu H-KG, Schreibmann E, Neill S G, Hadjipanayis C G, Holder C A, Shim H. A systematic pipeline for the objective comparison of whole-brain spectroscopic MRI with histology in biopsy specimens from grade III glioma. Tomography 2016; 2(2):106-116; and Cordova J S, Shu H-K G, Liang Z, Gurbani S S, Cooper L A D, Holder C A, Olson J J, Kairdolf B, Schreibmann E, Neill S G, Hadjipanayis C G, Shim H. Whole-brain spectroscopic MM biomarkers identify infiltrating margins in glioblastoma patients. Neuro Oncol 2016; 18(8):1180-1189. In some embodiments, other protocols additionally and/or alternatively may be used, such as point-resolved spectroscopy sequence (PRESS), simultaneous echo sequence (STEAM), among others, or any combination thereof.

In some embodiments, the MR spectroscopy data may be pre-processed multi-voxel MR spectroscopy data. In some embodiments, the multi-voxel MR spectroscopy data may be represented by or provided in a (first) matrix that includes a plurality of datapoints (or components) for each spectrum of each voxel. The matrix may be a 2D matrix in which each row represents a spectrum. For example, the plurality of datapoints or components of the first matrix may represent the entire spectrum model of each voxel in a region of interest. In some examples, the matrix may include 512 datapoints or components of the spectrum for each voxel. However, the matrix may include less or more datapoints/components of the (entire) spectrum for each voxel.

In some embodiments, the step 110 may include processing the data acquired by the acquisition device to prepare the MR spectroscopy data for the neural network system. For example, the (original) MR spectroscopy data may be processed so that a plurality of datapoints representing the (entire) spectrum model is in a form of the (first) matrix. By of example, the MR spectroscopy data (e.g., free-induction decays or partially processed into time or frequency domain data) received from the MR acquisition device be further processed to generate resonance frequency domain data for each spectrum, if necessary, and the matrix may be generated using the resonance frequency domain data from the region of interest.

In some embodiments, the method 100 may include a step 120 of processing the (entire) MR spectroscopy dataset (e.g., first matrix) through a first neural network of a series of neural networks to generate one or more baseline components. The baseline components or datapoints of each spectrum may represent the baseline model of the spectrum for each voxel.

The first neural network may include a trained encoder and a decoder. The trained encoder may determine a plurality of baseline parameters for each spectrum/voxel and the decoder may be defined by a mathematical technique to convert/determine the baseline component(s) (or datapoints) using the baseline parameters for each spectra. The mathematical technique may include but is not limited to one or more wavelet reconstruction equations. In some embodiments, the baseline parameters can represent local and non-local oscillations in the signal, enabling modeling by the decoder of the overall shape of the spectrum not including the metabolite peaks. The baseline parameters may be specific to the mathematical technique(s) used in the decoder.

In some embodiments, the baseline components/datapoints for each voxel may be disposed in a matrix (also referred to as a "second matrix"). In some embodiments, the second matrix may include the same number of baseline components/datapoints for each voxel as the first matrix (e.g., inputted data provided in step 110). The baseline components of each spectrum of the second matrix may represent the baseline model for the respective voxel that does not include the metabolite peaks (i.e., the peak model).

Next, the method 100 may include a step 130 of generating a baseline-corrected spectra data for each spectrum/voxel. By of example, the step 130 may include subtracting the baseline components for each spectrum (second matrix from step 120) from the inputted data set (the first matrix from step 110) to determine base-line corrected data for each spectrum.

In some embodiments, the baseline-corrected components/datapoints of each spectrum may be disposed in a matrix (also referred to as a "third matrix") for the respective voxel. In some embodiments, the third matrix may be a 2D matrix that includes the same number of components/datapoints and rows (corresponding to the spectra) as the first matrix (e.g., inputted data provided in step 110) and the second matrix (e.g., step 120).

In some embodiments, the method 100 may include a step 140 of determining peak components for each spectrum of each voxel using a second neural network of the series and the baseline-corrected components/datapoints. In some embodiments, the second neural network may include a trained encoder and a decoder. The trained encoder may determine a plurality of peak parameters for each spectra and the decoder may be defined by line-shape equations to determine peak components for each spectrum. In some embodiments, the line-shape equations may include but is not limited to Lorentzian-Gaussian lineshape model equations.

In some embodiments, the peak components of the spectrum for each voxel may include components/datapoints representing one or more peak regions associated with one or more metabolite resonances of the one or more of the metabolite(s) to be measured. The peak components for each voxel may define the peak model of its respective spectrum and may be represented or disposed in a matrix (may be referred to as a "fourth matrix"). In some embodiments, the fourth matrix may be a 2D matrix that includes the same number of rows and components/datapoints as the other (first, second and third) matrices.

In some embodiments, the plurality of peak parameters may include one or more peak parameters specific to each metabolite to be measured and/or peak region/spectral features of each spectrum. By way of example, the plurality of peak parameters may include but is not limited to amplitude of a peak region associated each metabolite to be measured, frequency shift associated with that peak region, zero-order phase, first-order phase, Gaussian decay constant, Lorentzian decay constant, among others, or a combination thereof.

In some embodiments, the method 100 may optionally include adding the outputs (second and fourth matrices) from steps 130 and 140 to generate a fitted spectrum for each voxel. Each generated fitted spectrum may be compared to the inputted spectrum for each voxel (first matrix from step 110) to ensure a proper fit, for example, using a root-mean-squared error, for that voxel. In a trained model, the measurement of proper fit for each spectrum can be used to determine whether or not the data for that spectrum are reliable and should be used in clinical decision making. By way of example, if the method determines that there is not a proper fit (e.g., the root mean-squared error for a spectrum is above a threshold), the method 200 may not include this spectrum in the one or more metabolite measurements, alert the clinician, among others, or a combination thereof. In some embodiments, an average of the calculated error for a batch of the spectra can additionally or alternatively be used to update the weights of the encoders of the first and second neural networks.

In some embodiments, the method 100 may include a step 150 of determining one or more measurements of the one or more metabolites for the region of interest using the peak components of each spectrum (e.g., represented by the fourth matrix). In some embodiments, the step 150 may including determining one or more spectral features associated with each peak region of each spectrum. The one or more spectral features may include peak maximum value, a power value, a value of the area under the curve, a full width at half maximum value, among others, or a combination thereof.

In some embodiments, the one or more measurements may include quantification of a concentration of one or more metabolites, among others, or a combination thereof. By way of example, the concentration may include concentration of one metabolite, a concentration ratio of two or more metabolites, among others, or a combination thereof. In some embodiments, the one or more measurements may be with adjusted, for example, with respect to voxel volume.

For example, for evaluating glioblastoma, the one or more measurements may include one or more metabolite combinations, such as Cho/NAA. By way of example, the one or more metabolite combinations may include the Cho/NAA abnormality index (Cordova J S, Shu H-K G, Liang Z, Gurbani S S, Cooper L A D, Holder C A, Olson J J, Kairdolf B, Schreibmann E, Neill S G, Hadjipanayis C G, Shim H. Whole-brain spectroscopic MIII biomarkers identify infiltrating margins in glioblastoma patients. Neuro Oncol 2016; 18(8):1180-1189) and the Cho-NAA-index (McKnight T R, von dem Bussche M H, Vigneron D B, Lu Y, Berger M S, McDermott M W, Dillon W P, Graves E E, Pirzkall A, Nelson S J. Histopathological validation of a three-dimensional magnetic resonance spectroscopy index as a predictor of tumor presence. Journal of Neurosurgery 2002; 97(4): 794-802). The Cho/NAA abnormality index may correspond to the measured Cho/NAA of a given voxel divided by the mean Cho/NAA value in contralateral in normal-appearing white matter (NAWM).

In some embodiments, the method 100 may include a step 160 of outputting the one or more measurements of one or more metabolites for the region of interest, for example, for further processing, transmitting, and/or storing (e.g., an electronic record system such as PACs). In some embodiments, the outputting may include registering the metabolite measurement(s) with clinical anatomical MRI data, for example, to generate a map. For example, volumes can be co-registered using a rigid transformation and resampled (e.g., using trilinear interpolation into a high-resolution T1w image space), enabling overlays of the metabolic measurement(s) (information) onto the anatomic MRI. This map can enable a visual assessment of metabolic changes in spatially dependent manner. In some examples, a clinician can select a voxel on the map to bring up the corresponding spectrum.

In some embodiments, the one or more measurements may be used within a clinical workflow. For example, the one or more measurements may be used to generate a radiation plan for radiation therapy, target planning for surgical biopsy and/or resection, diagnosis indication of a medical condition (e.g., tumor, brain traumatic injury, etc.), among others, or a combination thereof. For example, for radiation therapy planning, the one or more measurements may be integrated with clinical 3D MRI volumes, enabling clinicians to evaluate relevant metabolite levels and the underlying spectra used for this quantitation, to delineate target volumes for radiation therapy planning based on this information, among others, or any combination thereof. By way of example, clinicians can delineate target volumes based on both anatomic and spectroscopic information on the generated maps. These targets can be exported as Digital Imaging and Communication in Medicine (DICOM) radiation therapy structure sets (DICOM RT) or binary DICOM masks and imported into radiation therapy planning systems to deliver therapy to patients.

In some embodiments, the one or more measurements may be compared to one or more thresholds to generate a diagnosis indication.

Figure 2:
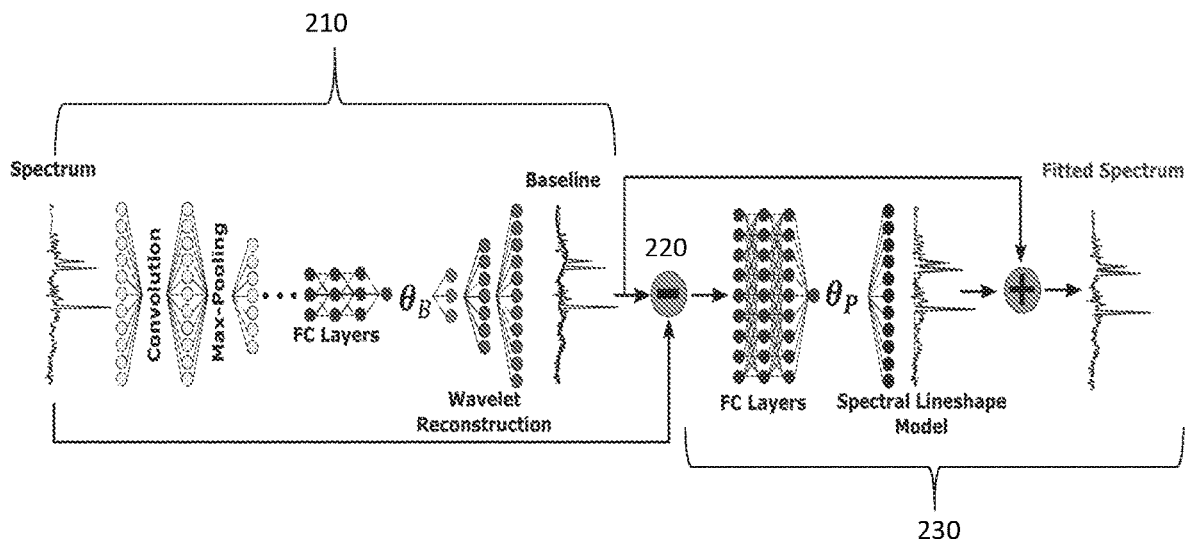
FIG. 2 shows an example of a neural network architecture according to embodiments.

FIG. 2 shows an example 200 of the neural network architecture according to embodiments. In some embodiments, the neural network architecture 200 may include two serial encoder-decoder stages: a first (convolutional) neural network 210 for determining baseline components for each voxel/spectrum and a second (convolutional) neural network 230 for determining peak components representing peak model for each respectively voxel/spectrum. In some embodiments, the (first) matrix of the plurality of the spectra/voxels may be passed through the first neural network 210 to determine a plurality of baseline parameters/coefficients (also referred to as "wavelet coefficients") $\theta_B$. Next, the decoder of the first neural network 210 may use the baseline parameters to determine the one or more baseline components using a wavelet reconstruction technique. As shown, the baseline components in a form of a second matrix may be subtracted from the input/first matrix (220).

Then, each baseline-corrected/baseline-subtracted spectrum may pass through the second (convolutional) neural network 230 to compute the peak parameters (also referred to as "metabolite resonance peak parameters"), $\theta_P$. In some examples, the encoder for the second neural network 230 may determine six parameters: peak amplitude $A_m$ for each metabolite m to be measured, resonance frequency $\omega_m$ for each metabolite m to be measured, zero and first order phases ($\phi_0$ and $\phi_1$), and Gaussian and Lorentzian decay constants ($T_a$ and $T_b$). For example, for evaluating glioblastoma, the metabolites (m) to be measured may include Cho, Cr, and NAA. Next, an estimate of the peak components, which may refer to metabolite resonances, $\vec{s}_{peak}$, can be determined by the decoder of the network 230 using a Lorentzian-Gaussian lineshape model. Using the peak components, one or more measurements (e.g., a concentration of each metabolite resonance) may be determined.

In some embodiments, the baseline and resonance peak components can be added together to produce an estimate of the fitted spectrum, $\vec{s}_{fit}$. The root-mean-squared error (RMSE) of the input and fitted spectrum can be used to update the weights of the encoders for CNN 210 and 230, for example, using gradient backpropagation.

Example

A system including convolutional neural network encoders with model-based decoding of the spectrum was constructed to incorporate various aspects of the embodiments disclosed herein and were used and evaluated for the fitting of singlet resonances in MRSI of the brain and for the generation of metabolite maps of interest. Metabolite maps generated using this system were then compared with those produced by existing parametric spectral fitting method, the FITT program of the Metabolite Imaging and Data Analysis System (later referred to as "MIDAS") (Maudsley A A, Domenig C, Govind V, Darkazanli A, Studholme C, Arheart K, Bloomer C. Mapping of brain metabolite distributions by volumetric proton MR spectroscopic imaging (MRSI). Magn Reson Med 2009; 61(3):548-559; and Sabati M, Sheriff S, Gu M, Wei J, Zhu H, Barker P B, Spielman D M, Alger J R, Maudsley A A. Multivendor implementation and comparison of volumetric whole-brain echo-planar MR spectroscopic imaging. Magn Reson Med 2015; 74(5):1209-1220) (17, 18), which uses iterative time-frequency parametric modelling methods for spectral analysis (Soher B J, Young K, Govindaraju V, Maudsley A A. Automated spectral analysis III: application to in vivo proton MR spectroscopy and spectroscopic imaging. Magn Reson Med 1998; 40(6): 822-831).

Methods

Image Acquisition and Processing

Volumetric echo planar spectroscopic imaging (EPSI) scans were performed on four healthy subjects and six subjects with newly diagnosed glioblastoma who were enrolled in an ongoing clinical trial (NCT03137888). Scans were conducted at 3T (Siemens Prisma) with a 32-channel head coil (Siemens Healthineers, Erlangen, Germany). For the subjects with glioblastoma, data were obtained following surgical resection but prior to radiation therapy and chemotherapy, as previously described (Gurbani S S, Schreibmann E, Maudsley A A, Cordova J S, Soher B J, Poptani H, Verma G, Barker P B, Shim H, Cooper L A D. A convolutional neural network to filter artifacts in spectroscopic MRI. Magnetic Resonance in Medicine 2018; 80(5):1765-1775). Briefly, T1-weighted (T1w) magnetization-prepared rapid gradient echo pulse (TR=1900 ms, TE=3.52 ms, 256×256× 160 matrix, flip angle (FA)=9°) and whole-brain 3D EPSI (TR=1551 ms, TE=50 ms, 64×64×32 matrix, FA=71°) sequences with generalized autocalibrating partially parallel acquisitions (GRAPPA) acceleration were obtained during the same scanning session, oriented at a +15 degree tilt in the sagittal plane from the anterior commissure-posterior commissure line (Griswold M A, Jakob P M, Heidemann R M, Nittka M, Jellus V, Wang J, Kiefer B, Haase A. Generalized autocalibrating partially parallel acquisitions (GRAPPA). Magnetic Resonance in Medicine: An Official Journal of the International Society for Magnetic Resonance in Medicine 2002; 47(6):1202-1210). For the EPSI/GRAPPA sequence, an oblique saturation band was placed in the sagittal plane from the optic chiasm to the cerebellum. A medium TE of 50 ms was used to reduce the impact of lipid contamination and emphasize the signal of metabolites of interest in subjects with brain tumors: choline (Cho), creatine (Cr), and N-acetylasparate (NAA). MIDAS (Maudsley A A, Domenig C, Govind V, Darkazanli A, Studholme C, Arheart K, Bloomer C. Mapping of brain metabolite distributions by volumetric proton MR spectroscopic imaging (MRSI). Magn Reson Med 2009; 61(3):548-559; and Sabati M, Sheriff S, Gu M, Wei J, Zhu H, Barker P B, Spielman D M, Alger J R, Maudsley A A. Multivendor implementation and comparison of volumetric whole-brain echo-planar MR spectroscopic imaging. Magn Reson Med 2015; 74(5):1209-1220) was used to perform the following preprocessing and volume reconstruction steps: spatial reconstruction, B0 field correction using simultaneously-acquired intracellular water signal, co-registration of the T1w and metabolite volumes, lipid suppression, and water suppression. The initial processing also created a mask covering the brain volume, but excluding voxels for which the water linewidth was greater than 18 Hz, as calculated using the T2* map. A total of 102,005 spectra were obtained and separated into three data subsets: 85,661 for training; 8,192 for validation; and 8,192 for testing.

For assessing generalizability, additional data from subjects with newly-diagnosed glioblastoma that were scanned at Emory University, the University of Miami and the Johns Hopkins University, were evaluated. The same sequences and parameters as above were used, with the exception that studies at the University of Miami were carried out on a 3T Siemens Skyra with a 20-channel head coil.

Convolutional Encoder—Model Decoder

The goal of spectral fitting for an input spectrum, $s \in \mathbb{R}^{512}$, is to find a parameter set, $\theta \in \mathbb{R}^k$, $k \ll 512$, such that when these parameters are used in a spectral model, $g(\theta)$, the result is a noise-free approximation of the input:

$$g(\theta): \mathbb{R}^k \to \mathbb{R}^{512}, g(\theta) \approx s \quad (1)$$

Mathematically, this can be represented as the following optimization task:

$$\operatorname*{argmin}_{\theta}[g(\theta) - s] \quad (2)$$

Figure 3:
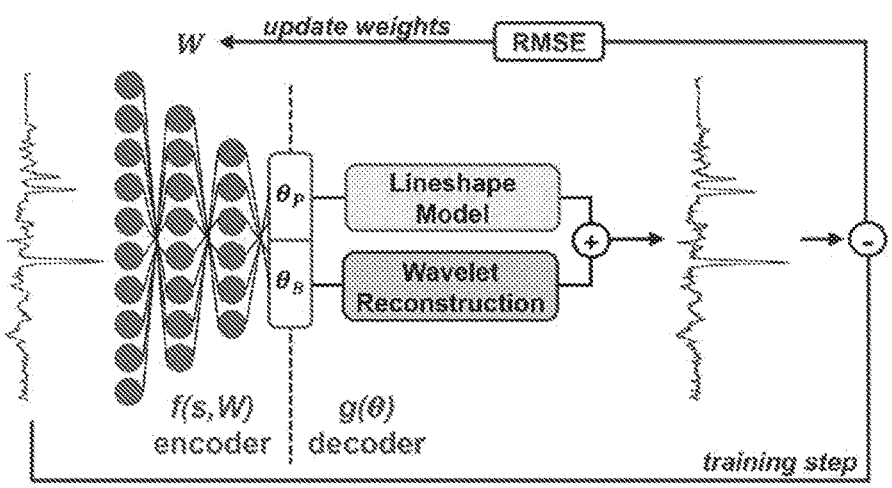
FIG. 3 is an illustrative example of the training of the neural network architecture according to embodiments.

In this context, the task of finding θ is the encoding step while the function $g(\theta)$ is the decoding step. FIG. 3 shows a graphical depicted example of the convolutional encoder-model decoder (CEMD) architecture to be trained according to embodiments. The encoding steps in CEMD may be a convolutional neural network (CNN) composed of sequential layers of convolution, pooling, and rectification (Wei Dai CDSQJLSD. Very Deep Convolutional Neural Networks for Raw Waveforms. 2016; Goodfellow I, Bengio Y, Courville A. Deep Learning: MIT Press; 2016. 800 p). Each of these layers may have parameterized weights that can collectively be referred to as W; therefore, the CNN with weights W can be conceived of as applying a series of transformations that perform the encoding function $f$: $\mathbb{R}^{512} \to \mathbb{R}^k$ defined by $f(s,W)=\theta$. Training can identify W to minimize the error defined in Equation 2. In the context of spectral fitting, a fixed spectral model can be used as the decoder (Equation 1) to generate a fitted version of the input spectrum. The overall training objective can be stated as:

$$\operatorname*{argmin}_{W}[g(f(s, W)) - s] \quad (3)$$

This optimization required no "ground truth" or "true" fitted spectra for the CNN training. It can be an unsupervised learning task requiring only a set of spectra, $S=\{s_1, s_2, \ldots, s_N\} \in \mathbb{R}^{512 \times N}$, to train the CNN weights with the goal of minimizing the residual error between the input data and fitted spectra.

The decoders may model a spectrum as having two components: i) metabolite resonances that are explicitly defined, and ii) a baseline composed of all metabolites and macromolecules not explicitly defined (Young K, Soher B J, Maudsley A A. Automated spectral analysis II: application of wavelet shrinkage for characterization of non-parameterized signals. Magn Reson Med 1998; 40(6):816-821; and Soher B J, Young K, Govindaraju V, Maudsley A A. Automated spectral analysis III: application to in vivo proton MR spectroscopy and spectroscopic imaging. Magn Reson Med 1998; 40(6):822-831). Metabolite resonances were modeled using the Lorentzian-Gaussian lineshape model:

$$s = FFT\left(\sum_{m=1}^{3} A_m e^{-i(\omega_{m,0}+\Delta\omega_m+\phi_1)t+\phi_0} e^{-\left[\frac{t}{T_a}+\left(\frac{t}{T_b}\right)^2\right]}\right) \quad (4)$$

For each metabolite, m, the metabolite model required six parameters: peak amplitude $A_m$, resonance frequency $\omega_m$, zero and first order phases ($\phi_0$ and $\phi_1$), and Gaussian and Lorentzian decay constants ($T_a$ and $T_b$). The three major singlet resonances at TE=50 ms were modeled: Cho, Cr, and NAA. Note that this formulation returned the relative concentrations of each metabolite, not the peak area. A constraint was placed such that all three metabolites have the same zero- and first-order phase shifts and linewidths, such that only the resonance frequency and amplitude needed to be independently determined. Since the expected resonance frequency, defined as $\omega_{m,0}$, is known a priori from a library of chemical resonances, only a shift in frequency from the expected, $\Delta\omega_m$, needed to be calculated. Thus, for these three metabolite singlet resonances, a total of 10 parameters were needed:

$$\theta_P = \{A_{Cho}, A_{Cr}, A_{NAA}, \Delta\omega_{Cho}, \Delta\omega_{Cr}, \Delta\omega_{NAA}, \phi_0, \phi_1, T_a, T_b\} \quad (5)$$

The baseline component was defined by wavelet reconstruction, using a set of coarse (Donoho D L, Johnstone I M. Adapting to Unknown Smoothness via Wavelet Shrinkage. J Am Stat Assoc 1995; 90(432):1200-1224) third-order Coiflets (Daubechies I. Ten lectures on wavelets: Siam; 1992) as the wavelet kernels and four levels of dyadic upsampling to convert 32 coarse coefficients ($\theta_B$) into the baseline signal. In order to enable automated computation of gradients for training the CNN in TensorFlow (Abadi M, Barham P, Chen J, Chen Z, Davis A, Dean J, Devin M, Ghemawat S, Irving G, Isard M. Tensorflow: a system for large-scale machine learning. 2016. p 265-283), wavelet reconstruction was implemented as a series of linear matrix operations. At each level, the output of the previous iteration, $y_{low} \in \mathbb{R}^P$, were first dyadically upsampled (Strang G, Nguyen T. Wavelets and filter banks: SIAM; 1996). Dyadic upsampling on a vector y was implemented as augmentation of its transpose with a vector of zeros of the same size, followed by vectorization and transposition:

$$y = [y_1 \ \ldots \ y_P] \qquad (6)$$

$$y^{aug} = (y^T | \vec{0}_P)^T = \left(\begin{bmatrix} y_1 & 0 \\ \vdots & \vdots \\ y_P & 0 \end{bmatrix}\right)^T = \begin{bmatrix} y_1 & \ldots & y_P \\ 0 & \ldots & 0 \end{bmatrix} \qquad (7)$$

$$y^{up} = vec(y^{aug})^T = [y_1 \ 0 \ y_2 \ 0 \ \ldots \ y_P \ 0] \qquad (8)$$

The upsampled vector was then convolved with the Coiflet low-frequency reconstruction kernel, $Coif3_{low}$ (Daubechies I. Ten lectures on wavelets: Siam; 1992):

$$y'_{low} = y_{low}^{up} * Coif3_{low} \qquad (9)$$

The central 2p elements of $y'_{low}$ were used as the input for the next level of wavelet reconstruction. The CEMD encoder therefore needed to calculate 42 coefficients, 10 for the metabolite resonances and 32 for the baseline, which are passed to the decoder to create the fitted spectrum.

As shown in FIG. 2, only the real component of the complex input spectrum ($s \in \mathbb{R}^{512}$) could be passed through a CNN during the encoder to produce a low-rank representation that directly corresponded to the 42 spectral model parameters. The decoder then applied the metabolite resonance and baseline models to the low-rank representation and created the fitted spectrum ($s' \in \mathbb{R}^{512}$). The training set consisted of N=85,661 frequency domain spectra each consisting of 512. The mean and standard deviation of the amplitude, $\mu_{train}$ and $\sigma_{train}$, were computed across the entire set, and each input spectrum, $\vec{s}$, was normalized as:

$$\vec{s}_{norm} = \frac{\vec{s} - \mu_{train}}{4 * \sigma_{train}} \qquad (10)$$

While CEMD followed an encode-decode scheme, it can include two serial encoder-decoder stages. First, the normalized spectrum, $\vec{s}_{norm}$, was passed through a CNN that computed the 32 coarse wavelet coefficients, $\theta_B$. This CNN included 13 convolution layers, with max-pooling after the $4^{th}$, $8^{th}$, and $13^{th}$ layers, followed by two fully-connected (FC) layers (Goodfellow I, Bengio Y, Courville A. Deep Learning: MIT Press; 2016. 800 p; and LeCun Y, Bengio Y, Hinton G. Deep learning. Nature 2015; 521(7553):436-444). An estimate of the baseline, $\vec{s}_{baseline}$, was made from the decoder using the wavelet reconstruction technique described in Equations 5-9. Next, the baseline was subtracted from the input spectrum:

$$\vec{s}_{sub} = \vec{s}_{norm} - \vec{s}_{baseline} \qquad (11)$$

The baseline-subtracted spectrum, $\vec{s}_{sub}$, was passed through a second CNN having 6 fully-connected layers that computed the metabolite resonance peak parameters, $\theta_p$. An estimate of the metabolite resonances, $\vec{s}_{peak}$, was made by the decoder using Equation 4. Next, the baseline and resonance peak estimates were added together to produce an estimate of the fitted spectrum, $\vec{s}_{fit}$. The root-mean-squared error (RMSE) of the input and fitted spectrum was used to update the weights of the encoder CNN, and was calculated as:

$$s_{resid} = \sum_{i=1}^{512} |s_{norm,i} - s_{fit,i}| \qquad (12)$$

CEMD was developed in the Python programming language using the TensorFlow 1.3 (Google LLC, Mountain View, CA) library, and trained using TensorFlow's Adam optimizer (Kingma D P, Ba J. Adam: A Method for Stochastic Optimization. 3rd International Conference for Learning Representations. San Diego, CA, USA 2015) on a high-end workstation with two Titan X graphical processing units (GPUs; Nvidia Corporation, Santa Clara, CA).

In each epoch of training, spectra in the training data set were run through CEMD to produce fitted spectra, RMSE for each spectrum was calculated, and gradient backpropagation was performed to update the encoder weights. Then, the spectra in the validation set were run through the CEMD and the validation loss was calculated as the sum of RMSEs. Training continued through multiple epochs until the validation loss converged. Once the autoencoder was trained and the CNN weights finalized, the testing set was used to determine final statistics of CEMD performance. The RMSE was calculated for each spectrum in the testing set, and the mean and standard deviation were reported. Once training of the CEMD encoder weights was complete, the encoder can be applied to spectra to compute the relative concentration of each metabolite resonance based on the parameters in the encoder output, $\theta_p$.

Whole-Brain Mapping

A software pipeline to perform CEMD fitting on whole-brain MRSI and to generate volumetric metabolite and ratios maps was developed. Only voxels within the region defined from the brain mask were analyzed, for both the CEMD and MIDAS fitting. While training of the CNN required a GPU, the final CEMD was implemented on a central processing unit (CPU) architecture consisting of a four-core CPU. To assess the utility of generated volumetric for radiation treatment planning, the Cho/NAA ratio map was computed for 10 subjects with glioblastoma fitted by CEMD and an existing parametric analysis method implemented in MIDAS. Spectral fitting in MIDAS used the METAFIT option, which applies three applications of fitting (the FITT program). First, B0 and phase corrections are performed, prior to applying a spatial smoothing and fitting of a higher-SNR copy of the data. Using the initial values from this intermediate result a final spectral analysis is performed on the original spectra. After fitting, voxels were excluded from both sets of results based on spectral outlier filters, namely those having values that are more than four standard deviations from the mean value within the brain.

Identification of abnormal Cho/NAA regions was determined from the results of each fitting method using the largest single connected component of voxels that had a Cho/NAA at least twofold increased compared to the mean value in contralateral normal-appearing white matter; this particular threshold was previously determined to be optimal for identifying high-risk regions for disease recurrence (20, 100, 113). The identified regions from each result were compared using the Dice similarity coefficient (DSC) (129) and a Z test was performed for each subject using the logit transform of the DSC (130).

Results

Training time for the CEMD was approximately 4 hours using TensorFlow on a workstation with two Nvidia Titan X GPUs. The testing set achieved a mean RMSE of fit of 5.0% normalized to the amplitude of the largest peak in each spectrum in the testing set, with a standard deviation of 0.6%. Sample spectra from the testing set are shown in FIGS. 4A-D with the baseline and peak+baseline fit overlaid on the input spectra. CEMD can handle a variety of baseline effects, varying from a relatively flat baseline near the peaks of interest, as shown in FIG. 4A, to major shifts that can occur at frequencies in the region of lipid or metabolites FIG. 4B. Phases can also be determined by the model as shown in FIGS. 4C and D. Even if the signal-to-noise ratio is poor, due to partial volume effects, magnetic field inhomogeneity, or receiver coil sensitivity, CEMD can identify and fit the peak and baseline components.

Sample spectra from three subjects with glioblastoma, not included in the training, testing, or validation sets, are shown in FIGS. 5A-F. In patients with glioblastoma, voxels within the region of active tumor exhibit an increase in Cho and a concomitant decrease in NAA (20). The CEMD-fitted spectra (black) are overlaid on the input spectra (gray). Subject one (FIGS. 5A and B) was scanned at Emory University; subject two (FIGS. 5C and D) was scanned at the University of Miami; and subject three (FIGS. 5E and F) was scanned at the Johns Hopkins University. All three subjects were scanned using the protocol defined in the Methods section, and data were preprocessed in MIDAS as described. Spectra in the left column (FIGS. 5A, C and E) are from voxels in the contralateral normal-appearing hemisphere, while spectra in the right column (FIGS. 5B, D and F) are taken from voxels in regions of tumor.

FIGS. 6A-D show a comparison of metabolite values computed by MIDAS and CEMD. FIGS. 6A-C show correlations between the metabolite concentrations of Cho, Cr, and NAA, respectively, calculated by CEMD and MIDAS for the testing set; and FIG. 6D shows the correlation between the Cho/NAA ratio, calculated by CEMD and MIDAS for the testing set. The solid lines plot the mean value between the two fitting techniques for each bin of values, and the shaded region around the line indicates +/−1 standard deviation. Overlaid in light gray are the histograms for the distribution of metabolite values computed by MIDAS. The variance of CEMD predictions compared to MIDAS is inversely correlated with the number of training samples available. While the two algorithms are linear in the regions where most of the data are present, CEMD has greater uncertainty at the tail end of the histograms where there were fewer training data.

FIGS. 7A-D show a comparison of CEMD and MIDAS spectral fittings on four challenging spectra. Spectra were taken from patients with glioblastoma. a.u.=arbitrary units. The first (FIG. 7A) depicts a spectrum with a large baseline shift on the right-side of the NAA peak. The second (FIG. 7B) shows a spectrum with a large decline of the baseline on the Cho and Cr peaks but a flat baseline near the NAA peak. The third (FIG. 7C) shows a spectrum from a voxel near the inferior rim of the surgical cavity, where partial volume effects reduce the apparent signal-to-noise ratio and where there is an absence of the NAA peak at 2.0 ppm. The fourth (FIG. 7D) depicts a spectrum from the bone-cortex interface in the temporal; all peaks have broadened linewidth and the NAA peak is adjacent to large noise and lipid signal. All results show comparable performance for fitting of the metabolite peaks with some differences in the baselines.

Results of the CEMD analysis for studies of a subject with glioblastoma, not included in the training set, are shown in FIG. 8, which shows the individual metabolite maps, the Cho/NAA ratio map, and corresponding contrast-enhanced T1-weighted (CE-T1w) and fluid-attenuated inversion recovery (FLAIR) MM volumes. Superimposed on the CE-T1w image is a contour drawn by a neuroradiologist to indicate contrast enhancing tissue and the surgical cavity, regions that would normally be targeted for high dose radiation therapy.

Cho/NAA abnormality volumes were contoured for CEMD and MIDAS fitting and the results are shown in table in FIG. 9, which includes subject-wise execution time, abnormality volumes, and DSC. The mean execution time for whole-brain spectral fitting was 20.6+/−2.8 sec using the CEMD. As a representative example, the execution time for CEMD on Subject 6 was broken down as follows: 2.7 seconds to load 11,702 spectra from disk into memory; 17.0 seconds to load the CEMD encoder model and to process all spectra; 3.3 seconds to create volumetric maps for each metabolite and the Cho/NAA ratio and to write these maps to disk. On average, CEMD-derived lesion volumes are larger by 1.2 $cm^3$ (P=0.83 using a two-tailed paired T test) and in several subjects encapsulated the contours produced from the MIDAS analysis. The mean DSC between CEMD and MIDAS was 0.72+/−0.13.

FIG. 10 show a comparison of Cho/NAA volumes computed by MIDAS and CEMD for Subject 9; FIG. 11 show regions A and B for comparison of Cho/NAA volumes of regions identified in respective computed by MIDAS and CEMD for Subject 1; and FIGS. 12 A and B show comparison of Cho/NAA volumes of regions A and B identified in respective computed by MIDAS and CEMD shown in FIG. 11 for Subject 1, respectively, were qualitatively compared. As shown, the contours indicate a twofold increase in Cho/NAA compared to contralateral white matter. Isolated bright spots are artifacts due to fitting errors and were not contoured. A spectrum from an area where the two algorithms had different values of Cho/NAA (box) is shown for each subject, with CEMD fit and MIDAS fit overlaid on the spectrum. Discrepancies occur either due to the calculated ratio being just above or below the 2× threshold (FIG. 11B), or in areas of minimal or poor signal quality and therefore the uncertainties in the measurements must be considered to be very high.

Discussion

In this example, a deep learning approach to spectral fitting that incorporates a priori spectral information was developed and evaluated. Spectral fitting is the computational bottleneck in processing of volumetric MRSI, largely because the existing methods are based on iterative algorithms. The CEMD is an unsupervised deep learning architecture that incorporates spectral models to generate an encoding of spectral parameters, which is advantageous because it does not require any "ground truth" spectral quantitation for training. The predictions of the CEMD have contextual meaning, and the CEMD was trained to make these predictions within the constraints of an explicitly defined spectral model. Once trained, the CEMD performs spectral fitting on volumetric data in under one minute using standard computer hardware. The order of magnitude improvement in fitting time can greatly benefit the clinical adoption of whole-brain MRSI. This architecture could be implemented on scanner computers, enabling real-time reconstruction and review of data without the need for offloading of data to more specialized computer systems. Fitted data and metabolite volumes could then easily be sent to a clinical PACS systems in a streamlined fashion.

CEMD can simultaneously compute the baseline and peak components of the spectrum and correctly identify singlets in challenging spectra such as those in FIG. 4. The spectrum in FIG. 4C indicates the loss of the NAA resonance at 2.0 ppm. It can be necessary for a fitting model understand where the NAA resonance should be and not attempt to model other peak-like shapes (e.g. at 2.3 ppm and 1.7 ppm) as NAA. For spectra where asymmetric broadening of peaks occurs, the spectral lineshape model can dictate that a symmetric peak should be fit (FIG. 4D). In these cases, CEMD performed on par with traditional parametric analysis algorithms such as that incorporated in MIDAS.

For this example, only the real part of the complex spectral data was used as input for CEMD and in the cost function for updating the CNN weights, though a complex spectral model (Equation 4) was used in the decoder.

While the CEMD was trained using data obtained on a single 3T scanner, data can be acquired using other pulse sequence parameters. To train the CEMD, for example, using different acquisition schemes, such as with shorter TE, training would not require many subjects because of the 10,000 spectra in each whole-brain scan. The CEMD could also be adapted, e.g. changing the number and type of layers in the encoder and number of coefficients in the decoder models, for more resonances, of multiplets of resonances, or of metabolites whose resonance peaks are not readily separable (gluatamate and glutamine). In general, because the autoencoder scheme does not rely on any external "ground truth" data, it can be readily adapted and optimized for different complexities of fitting.

In this example, a comparison between this new fitting paradigm and an existing iterative parametric optimization method was performed. The results in FIG. 6 show the correlation between the two algorithms' estimation of Cho, Cr, and NAA resonances and the Cho/NAA ratio on the same set of spectra. In spectroscopy, the acquired spectral signal amplitude is generally uncalibrated, and additional methods may be required to apply a signal normalization procedure. Ratios, such as Cho/NAA, do not require calibration; however, they can be more unstable when the denominator is low. As seen in FIG. 7D, both CEMD and MIDAS fitting have high uncertainty for high Cho/NAA values that represent low NAA regions. While individual metabolite resonance maps are shown in FIG. 8 to assess the ability of CEMD to perform whole-brain fitting, the Cho/NAA maps are used as the main comparison between CEMD and an existing parametric analysis (MIDAS) in the table shown in FIG. 9. CEMD can achieve a Dice coefficient of 0.72 when compared to MIDAS. A key observation is that CEMD can produce similar Cho/NAA volumes to MIDAS while never being trained to do so; thus, it independently can achieve similar results, which highlights the power of unsupervised learning techniques.

Conclusion

In this example, a machine learning approach to spectral fitting is described that can perform sub-minute calculation of relative metabolite concentrations in MRSI of the brain. A convolutional encoder-model decoder technique has been implemented that explicitly incorporates a parametric spectral model with the power of unsupervised feature-learning to produce fast spectral fittings that are constrained by the model. This can be a powerful paradigm that does not require a priori ground truth and relies upon spectral lineshape and baseline models to optimize the underlying convolutional neural network parameters. The CEMD architecture can produce accurate fitting of a variety of spectra acquired from multiple scanners in patients with glioblastoma, including correctly fitting challenging spectra with low SNR, partial volume effects, baseline shifts, phase shifts, and dropout of one or more metabolite resonances. The CEMD can fit whole-brain data on a standard multicore computer without the need for expensive workstations or GPUs, in less than one minute. With this new autoencoder-based neural network, the largest computational bottleneck in processing MRSI can be overcome, bringing improved performance that will support the implementation of MRS for more widespread clinical use.

System Architecture

Figure 13:
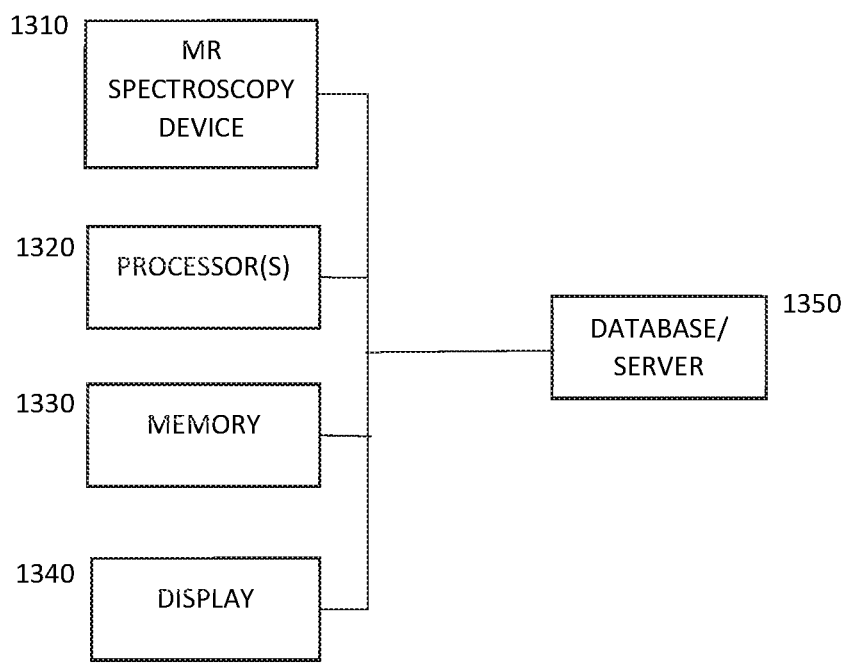
FIG. 13 shows a block diagram illustrating an example of a system according to embodiments.

FIG. 13 shows an example of a system 1300 for the determination of the one or more measurements of one or more metabolites. The system for carrying out the embodiments of the methods disclosed herein is not limited to the system shown in FIG. 13. Other systems may also be used. It is also to be understood that the system 1300 may omit any of the modules illustrated and/or may include additional modules not shown.

By way of example, the system 1300 may include a server 1350 and a computer system (e.g., processor 1320, memory 1330, and display 1340) or a MR spectroscopy acquisition system 1310 with the computer system. In another example, the system 1300 may be a computer or workstation instead of the medical scanner 1310, instead of the server 1350, or instead of both. In another example, the processor 1320, memory 1330, and display 1340 may be part of the system 1310. In further example, the processor 1320, the memory 1330, and the display 1340 may be a part of an archival and/or image processing system, such as associated with a medical records database workstation or server, or radiation therapy planning system, separate from the system 1310. In other examples, the processor 1320, the memory 1330, and the display 1340 may be a personal computer, such as a desktop or laptop, a workstation, or combinations thereof. The processor 1320, the display 1340, and the memory 1330 may be provided without other components for acquiring the MR spectroscopic data. By way of example, the acquisition system 1310 may be any MR spectroscopy acquisition system capable of obtaining MR anatomical and spectroscopic data, such as a MR system capable of proton spectroscopic magnetic resonance imaging.

The system 1300 shown in FIG. 13 may include any number of modules that communicate with each other through electrical or data connections (not shown). In some embodiments, the modules may be connected via any network (e.g., wired network, wireless network, or any combination thereof).

In some embodiments, the system 1300 may include one or more processors 1320. The processor(s) 1320 may include one or more processing units, which may be any known processor or a microprocessor. For example, the processor(s) may include any known central processing unit (CPU), imaging processing unit, graphical processing unit (GPU) (e.g., capable of efficient arithmetic on large matrices encountered in deep learning models), among others, or any combination thereof. The processor(s) 1320 may be coupled directly or indirectly to one or more computer-readable storage media (e.g., memory) 1330. The memory 1330 may include random access memory (RAM), read-only memory (ROM), disk drive, tape drive, etc., or any combinations thereof. The memory 1330 may be configured to store programs and data, including data structures. In some embodiments, the memory 1330 may also include a frame buffer for storing data arrays.

In some embodiments, another system may assume the data analysis, image processing, or other functions of the processor(s) 1320. In response to commands received from an input device, the programs or data stored in the memory 1330 may be archived in long term storage or may be further processed by the processor and presented on the display 1340.

In some embodiments, the disclosed methods and networks (e.g., FIGS. 1-3) may be implemented using software applications that are stored in a memory and executed by the one or more processors (e.g., CPU and/or GPU). In some embodiments, the disclosed methods may be implemented using software applications that are stored in memories and executed by one or more processors distributed across the system. If such acts are implemented in software, one or more processors of the associated computing system that performs the act direct the operation of the computing system in response to having executed computer-executable instructions. For example, such computer-executable instructions may be embodied on one or more computer-readable media that form a computer program product. An example of such an operation involves the manipulation of data. The computer-executable instructions (and the manipulated data) may be stored in the memory 1330, and/or in one or more separate computer system components (e.g., in a distributed computer system environment). The computer-executable instructions may be used to implement and/or instantiate all of the functionality disclosed herein, including the functionality that is disclosed in reference to the diagrams of FIGS. 1-3.

As such, any of the modules of the system 1300 may be a general-purpose computer system, that becomes a specific purpose computer system when executing the routines and methods of the disclosure. The systems and/or modules of the system 1300 may also include an operating system and micro instruction code. The various processes and functions described herein may either be part of the micro instruction code or part of the application program or routine (or any combination thereof) that is executed via the operating system.

If written in a programming language conforming to a recognized standard, sequences of instructions designed to implement the methods may be compiled for execution on a variety of hardware systems and for interface to a variety of operating systems. In addition, embodiments are not described with reference to any particular programming language. It will be appreciated that a variety of programming languages may be used to implement embodiments of the disclosure. An example of hardware for performing the described functions is shown in FIG. 13. It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other embodiments, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes but is not limited to portable or fixed storage devices, optical storage devices, wireless channels, and/or various other storage mediums capable of storing that contain or carry instruction(s) and/or data.

The disclosures of each and every publication cited herein are hereby incorporated herein by reference in their entirety.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A method for determining a concentration of one or more metabolites within a region of interest comprising:
    processing magnetic resonance (MR) spectroscopy data of a region of interest, the magnetic resonance spectroscopy data including a plurality of spectra of one or more metabolites, through a series of neural networks, the processing including:
        determining baseline components of each spectrum using a first neural network of the series, the baseline components defining a baseline model;
        generating baseline-corrected components for each spectrum using the baseline components; and
        determining one or more peak components of each spectrum using a second neural network of the series and the baseline-corrected components; and
    determining one or more metabolite measurements of the one or more metabolites in the region of interest using the one or more peak components.

2. The method of claim 1, further comprising:
    determining one or more spectral features of each peak region using the one or more peak components;
    wherein the one or more metabolite measurements are determined using the one or more spectral features.

3. The method of claim 2, wherein the one or more metabolite measurements includes a quantification of concentration of the one more metabolites, a concentration ratio between at least two metabolites, a chemical exchange rate between at least two metabolites, among others, or a combination thereof.

4. The method of claim 1, wherein:
    the region of interest is a portion of a brain; and
    the one or more metabolites includes choline (Cho) and N-acetylaspartate (NAA); and
    the one or more metabolite measurements includes a Cho/NAA ratio.

5. The method of claim 1, wherein:
    the first neural network includes a trained encoder and a decoder;
    the trained encoder determines a plurality of baseline parameters; and
    the decoder defined by wavelet reconstruction equations determines the baseline components for each spectrum using the baseline parameters.

6. The method of claim 5, wherein:
    the second neural network includes a trained encoder and a decoder; and
    the trained encoder determines a plurality of peak parameters; and
    the decoder defined by a Lorentzian-Gaussian lineshape model determines the peak components for each spectrum using the plurality of peak parameters.

7. The method of claim 6, wherein the one or more peak parameters includes one or more spectral features for each metabolite, zero-order phase, first-order phase, gaussian decay constant and Lorentzian decay constant.

8. The method of claim 1, further comprising:
    generating one or more maps of the region of interest using the one or more metabolites and/or one or more metabolite measurements and corresponding anatomical MR data.

9. The method of claim 8, further comprising:
    registering the one or more metabolites and/or the one or more metabolite measurements with the corresponding anatomical MR data.

10. The method of claim 1, wherein:
    the MR spectroscopy data is processed and provided in a first matrix, the matrix including a plurality of datapoints for each spectrum; the plurality of datapoints representing an entire model for each spectrum;
    the determining the baseline components includes generating a second matrix, the second matrix including the baseline components for each spectrum;
    the determining the baseline-corrected components includes generating a third matrix, the third matrix including the baseline corrected datapoints for each spectrum; and
    the determining the one or more peak components includes generating a fourth matrix, the fourth matrix including the one or more peak components for each spectrum.

11. A system for determining a concentration of one or more metabolites within a region of interest comprising:
    one or more processors; and
    one or more hardware storage devices having stored thereon computer-executable instructions which are executable by the one or more processors to cause the computing system to perform at least the following:
    processing magnetic resonance (MR) spectroscopy data of a region of interest, the magnetic resonance spectroscopy data including a plurality of spectra of one or more metabolites, through a series of neural networks, the processing including:
        determining baseline components of each spectrum using a first neural network of the series, the baseline components defining a baseline model;
        generating baseline-corrected components for each spectrum using the baseline components; and
        determining one or more peak components of each spectrum using a second neural network of the series and the baseline-corrected components; and
    determining one or more metabolite measurements of the one or more metabolites in the region of interest using the one or more peak components.

12. The system of claim 11, wherein the one or more processors are further configured to cause the computing system to perform at least the following:
- determining one or more spectral features of each peak region using the one or more peak components;
- wherein the one or more metabolite measurements are determined using the one or more spectral features.

13. The system of claim 12, wherein the one or more metabolite measurements includes a quantification of concentration of the one more metabolites, a concentration ratio between at least two metabolites, a chemical exchange rate between at least two metabolites, among others, or a combination thereof.

14. The system of claim 11, wherein:
- the region of interest is a portion of a brain; and
- the one or more metabolites includes choline (Cho) and N-acetylaspartate (NAA); and
- the one or more metabolite measurements includes a Cho/NAA ratio.

15. The system of claim 11, wherein:
- the first neural network includes a trained encoder and a decoder;
- the trained encoder determines a plurality of baseline parameters; and
- the decoder defined by wavelet reconstruction equations determines the baseline components for each spectrum using the baseline parameters.

16. The system of claim 15, wherein:
- the second neural network includes a trained encoder and a decoder; and
- the trained encoder determines a plurality of peak parameters; and
- the decoder defined by a Lorentzian-Gaussian lineshape model determines the peak components for each spectrum using the plurality of peak parameters.

17. The system of claim 16, wherein the one or more peak parameters includes one or more spectral features for each metabolite, zero-order phase, first-order phase, gaussian decay constant and Lorentzian decay constant.

18. The system of claim 11, wherein the one or more processors are further configured to cause the computing system to perform at least the following:
- generating one or more maps of the region of interest using the one or more metabolites and/or one or more metabolite measurements and corresponding anatomical MR data.

19. The system of claim 18, wherein the one or more processors are further configured to cause the computing system to perform at least the following:
- registering the one or more metabolites and/or the one or more metabolite measurements with the corresponding anatomical MR data.

20. The system of claim 11, wherein:
- the MR spectroscopy data is processed and provided in a first matrix, the matrix including a plurality of datapoints for each spectrum; the plurality of datapoints representing an entire model for each spectrum;
- the determining the baseline components includes generating a second matrix, the second matrix including the baseline components for each spectrum;
- the determining the baseline-corrected components includes generating a third matrix, the third matrix including the baseline-corrected datapoints for each spectrum; and
- the determining the one or more peak components includes generating a fourth matrix, the fourth matrix including the one or more peak components for each spectrum.

* * * * *